Sept. 15, 1959 R. V. LINDQUIST Plant Pat. 1,865
ROSE PLANT
Filed Jan. 2, 1959
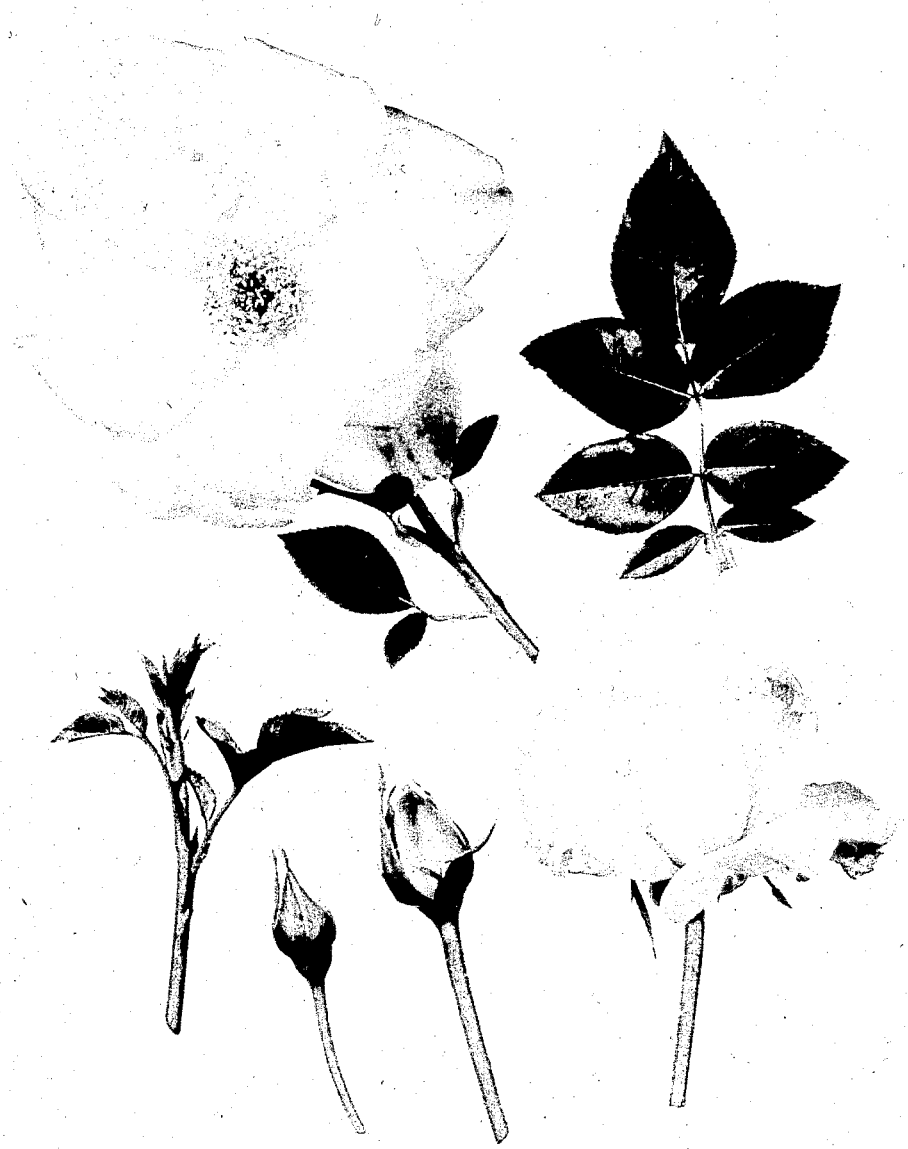
INVENTOR
R. V. Lindquist
BY Robb & Robb
ATTORNEYS United States Patent Office Plant Pat. 1,865
Patented Sept. 15, 1959

1,865

ROSE PLANT

Robert V. Lindquist, Hemet, Calif., assignor to Hemet Wholesale, Hemet, Calif., a partnership Application January 2, 1959, Serial No. 784,829

1 Claim. (Cl. 47—61)

The present invention relates to a new and distinct variety of rose plant of the hybrid tea class, which was originated by me by crossing the variety "Girona" (unpatented) with the variety "Golden Rapture" (unpatented).

As the result of this breeding, I have produced a new rose variety which is particularly characterized as to novelty by the following unique combination of characteristics which are outstanding in the new variety and which distinguish it from its parents, as well as from all other varieties of which I am aware:

(1) An unusual upright habit of growth;

(2) Perfect exhibition bud form;

(3) Heavy flower petal texture with attendant lasting-quality of the blooms and their ability to hold their shape until the petals drop; and (4) A very unusual blending of colors in both buds and open flowers.

Asexual reproduction of my new variety by budding, as performed at Hemet, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson" and Ridgway's Color Standards and Nomenclature (hereinafter abbreviated as "Ridgway"), except where general color terms of ordinary dictionary significance are obvious:

Type: Half-hardy; tall; bush; outdoor; seedling; for cut flowers and for garden decoration.

Class: Hybrid tea.

Breeding: Seedling.

*Seed parent.*—"Girona."

*Pollen parent.*—"Golden Rapture."

Propagation: Holds its distinguishing characteristics through succeeding propagations by budding.

*Flower*

Locality where grown and observed: Hemet, California.

Flowers borne: Usually singly; on stems of normal strength and medium length.

Quantity of bloom: Free, outdoors.

Continuity: Nearly continuous during growing season.

Fragrance: Moderate. Nature—tea.

Bud:

*Peduncle.*—Average length; average caliper; erect; moderately rough; few gland-tipped cilia; few prickles. Color—near Light Bice Green, Plate XVII (Ridgway).

*Before calyx breaks.*—Size—medium. Form—medium length; ovoid; with a conspicuous neck; with foliaceous appendages and few gland-tipped cilia; with foliaceous parts extending beyond the tip of the bud equal to ¼ or more of its length.

*As calyx breaks.*—Color—near Light Greenish Yellow, Plate V (Ridgway), with shadings of Pomegranate Purple, Plate VXII (Ridgway).

*Sepals.*—A sepal has either both margins covered or both uncovered except for the fifth or odd sepal, which has wooly tomentum on one margin only. Inner surface—with woolly tomentum. Glandular margins—usually with foliaceous appendages. Other margins—with woolly tomentum.

*As first petal opens.*—Size—average. Form—medium length; urn-shaped. Color: outside—base near Empire Yellow, Plate IV (Ridgway), shading to near Buff Yellow, Plate IV (Ridgway) and to near Cameo Pink, Plate XXVI (Ridgway) at edge of petal; inside—base near Lemon Chrome, Plate IV (Ridgway), shading to near Spinel Pink, Plate XXVI (Ridgway).

*Opening.*—Opens up well; is not retarded from opening by cold, hot, wet or dry weather.

Bloom:

*Size (when fully open).*—Averages from 4 inches to 5 inches.

*Petalage.*—Semi-double; from 20 to 25 petals, plus from 4 to 8 petaloids.

*Form.*—Cupped at first, but becoming from flat to open-cupped; petals being at first somewhat tightly cupped, with tips rolled outward, but becoming later at maturity somewhat loosely flat-cupped, with tips rolled outward.

Petals:

*Texture.*—Medium; moderately leathery. Inside—satiny. Outside—satiny.

*Shape.*—Outer—round; scalloped; with apex from rounded to flat; usually with 1 or 2 notches. Intermediate—round; scalloped; with apex from rounded to flat; with 1 or 2 notches. Inner—from nearly round to obovate; scalloped; with apex from rounded to flat; with 1 or 2 notches.

This description of a newly opened flower was made from a rose grown outdoors in the month of September at Hemet, California:

*Color.*—Outer petal: outside surface—base near Aureolin, Plate 3, page 3 (Wilson) and shading above to near Aureolin, Plate 3/2, page 3 (Wilson), and thence to near Thulite Pink, Plate XXVI (Ridgway); inside surface—base near Chrome Yellow, Plate 605, page 144 (Wilson), shading to near Spinel Pink, Plate XXVI (Ridgway). Intermediate petal: outside surface—base near Chrome Yellow, Plate 605, page 144 (Wilson), shading to near Apricot Yellow, Plate IV (Ridgway) in intermediate portions of the petal, with shadings of near Maize Yellow, Plate IV (Ridgway), and shading to near Cameo Pink, Plate XXVI (Ridgway) at outside edge of petal; inside surface—base near Chrome Yellow, Plate 605, page 144 (Wilson), shading to near Thulite Pink, Plate XXVI (Ridgway). Inner petal: outside surface—base near Chrome Yellow, Plate 605, page 144 (Wilson), shading to near Apricot Yellow, Plate IV (Ridgway) in intermediate portions of the petal, with shadings of near Maize Yellow, Plate IV (Ridgway), and shading to near Cameo Pink, Plate XXVI (Ridgway) at outside edge of petal; inside surface—base near Apricot Yellow, Plate IV (Ridgway), with shadings of near Maize Yellow, Plate IV (Ridgway), and shading to near Cameo Pink, Plate XXVI (Ridgway) at outside edge of petal.

This description was made from a rose that was open for 3 days in the month of September at Hemet, California:

*Color.*—Outer petal: outside surface—base near Aureolin, Plate 3, page 3 (Wilson) and shading above to near Aureolin, Plate 3/2, page 3 (Wilson), and thence to near Thulite Pink, Plate XXVI (Ridgway); inside surface—base near Chrome Yellow, Plate 605, page 144 (Wilson), shading to near Spinel Pink, Plate XXVI (Ridgway). Inner petal: outside surface—base near Chrome Yellow, Plate 605, page 144 (Wilson), shading to near Apricot Yellow, Plate IV (Ridgway) in intermediate portions of the petal, with shadings or near Maize Yellow, Plate IV (Ridgway), and shading to near Cameo Pink, Plate XXVI, (Ridgway) at outside edge of petal; inside surface—base near Apricot Yellow, Plate IV (Ridgway), with shadings of near Maize Yellow, Plate IV (Ridgway), and shading to near Thulite Pink, Plate XXVI (Ridgway) at outside edge of petal.

*General color effect.*—Nearly opened flower—near Apricot Yellow, Plate IV (Ridgway), shading to near Maize Yellow, Plate IV (Ridgway), and shading to near Spinel Pink, Plate XXVI (Ridgway) at outside edges of petals. 3-days open—near Apricot Yellow, Plate IV (Ridgway), shading to near Maize Yellow, Plate IV (Ridgway), and shading to near Thulite Pink, Plate XXVI (Ridgway) at outside edges of petals.

*Behavior.*—Drop off cleanly; not particularly affected by hot, wet or dry weather, but some changes in flower color during cold weather.

*Flower longevity.*—On bush in garden—3 or 4 days in September. Cut roses grown outdoors and kept at living-room temperatures—2 to 4 days in September.

*Reproductive Organs*

Stamens: Many; arranged regularly about pistils; a few mixed with petaloids.

Filaments: From short to medium length; occasionally a filament has a petaloid attached in place of anther; most with anthers. Color—near Buttercup Yellow, Plate 5/1, page 5 (Wilson).

Anthers: Medium size; all open approximately at once. Color: uper side—near Buttercup Yellow, Plate 5, page 5 (Wilson); under side—near Buttercup Yellow, Plate 5/2, page 5 (Wilson).

Pollen: Moderate. Color—near Buttercup Yellow, Plate 5, page 5 (Wilson).

Pistils: Average number; approximately 85 to 100 in number.

Styles: Moderately uneven; from short to average length; average calipers; somewhat bunched.

Stigma: Color—near Buttercup Yellow, Plate 5/3, page 5 (Wilson).

Ovaries: Usually most enclosed in calyx.

Hips: Average length; globular; moderately smooth; walls thick and fleshy. Color—near Deep Chrysolite Green, Plate XXXI (Ridgway).

Sepals: Falling soon; long; spear-shaped; recurved. Color: inside—near Corydalis Green, Plate XLI (Ridgway), modified by White tomentum; outside—near Light Bice Green, Plate XVII (Ridgway).

Seeds: Few; from 8 to 15 in number; usually medium size.

*Plant*

Foliage:

*Leaves.*—Compound of usually 3 to 7 leaflets; normal abundance; medium size; moderately heavy; somewhat leathery; semi-glossy.

*Leaflets.*—Shape—oval, with apex mucronate. Base—round. Margin—serrate.

*Color.*—Mature: upper surface—near Empire Green, Plate XXXII (Ridgway); under surface—near Light Elm Green, Plate XVII (Ridgway). Young: upper surface—near Light Bice Green, Plate XVII (Ridgway), with some near Corinthian Purple, Plate XXXVIII (Ridgway), becoming more intense toward margin; under surface—near Corinthian Purple, Plate XXXVIII (Ridgway), with some near Light Bice Green, Plate XVII (Ridgway).

*Rachis (the supporting stem of the compound leaf).*—Average size. Upper side—grooved, with some stipitate glands on edges. Under side—moderately prickly, and with few stipitate glands.

*Stipules.*—Long; medium width; with medium length points turning out at an angle of about 45°.

*Disease resistance.*—Average resistance to mildew, as determined by comparison wtih other varieties grown under comparable cultural conditions at Hemet, California.

Growth:

*Habit.*—Upright; moderately branched.

*Growth.*—Moderately vigorous.

*Canes.*—Medium caliper.

*Main stems.*—Color—near Bice Green, Plate XVII (Ridgway). Large prickles—several; medium length; hooked slightly downward; with moderately narrow base; Color—varying from near Sayal Brown, Plate XXIX (Ridgway) at base to near Cinnamon, Plate XXIX (Ridgway) at point. Small prickles—none. Hairs—none.

*Branches.*—Color—near Light Bice Green, Plate XVII (Ridgway). Large prickles—several; medium length; hooked slightly downward; with moderately narrow base; color—near Cinnamon, Plate XXIX (Ridgway). Small prickles—none. Hairs—none.

*New shoots.*—Color—near Light Bice Green, Plate XVII (Ridgway). Large prickles—several; medium length; hooked slightly downward; with moderately narrow base; color—near Courge Green, Plate XVII (Ridgway), shade at base to near Hellebore Red, Plate XXXVIII (Ridgway). Small prickles—none. Hairs—none.

I claim:

A new and distinct variety of rose plant of the hybrid tea class, substantially as herein shown and described, characterized particularly as to novelty by the unique combination of an unusual upright habit of growth, perfect exhibition bud form, heavy flower petal texture with attendant lasting quality of the blooms which hold their shape until the petals drop, and a very unusual blending of colors in both buds and open flowers.

No references cited.